United States Patent
Popov et al.

(10) Patent No.: US 9,993,468 B2
(45) Date of Patent: Jun. 12, 2018

(54) PHARMACEUTICAL COMPOSITION FOR TOPICAL APPLICATION

(75) Inventors: Todor Alexandrov Popov, Sofia (BG); Christo Tzachev Tzachev, Sofia (BG); Ivan Nedialkov Denev, Sofia (BG)

(73) Assignee: MOURAD MANKARIOS, Surrey BC (CA)

( * ) Notice: Subject to any disclaimer, the term of this patent is extended or adjusted under 35 U.S.C. 154(b) by 986 days.

(21) Appl. No.: 13/578,425

(22) PCT Filed: Nov. 18, 2009 (Under 37 CFR 1.47)

(86) PCT No.: PCT/IB2009/055140
§ 371 (c)(1),
(2), (4) Date: Sep. 23, 2013

(87) PCT Pub. No.: WO2010/058349
PCT Pub. Date: May 7, 2010

(65) Prior Publication Data
US 2014/0088134 A1 Mar. 27, 2014

(30) Foreign Application Priority Data
Nov. 21, 2008 (GB) .................... 0821298.7

(51) Int. Cl.
*A01N 43/42* (2006.01)
*A61K 31/44* (2006.01)
*A61K 31/4545* (2006.01)
*A61K 9/00* (2006.01)

(52) U.S. Cl.
CPC ........ *A61K 31/4545* (2013.01); *A61K 9/0043* (2013.01)

(58) Field of Classification Search
CPC .......................... A61K 31/4545; A61K 9/0043
See application file for complete search history.

(56) References Cited

U.S. PATENT DOCUMENTS

| 2007/0048384 A1 | 3/2007 | Rosenberg |
| 2007/0207201 A1 | 9/2007 | Krishman |
| 2007/0286875 A1* | 12/2007 | Dagar et al. ................ 424/400 |

FOREIGN PATENT DOCUMENTS

| WO | WO2003101434 A2 | 12/2003 | | |
| WO | WO2004082589 A2 | 9/2004 | | |
| WO | 2007/143382 A2 | 12/2007 | | |
| WO | WO 2008075102 A1 * | 6/2008 | ............. | A61K 9/006 |
| WO | WO 2010042701 A2 * | 4/2010 | ........... | A61K 9/0043 |

OTHER PUBLICATIONS

Rahman et al, Pharmazie Feb. 1999;54(2):132-6.*
International Preliminary Report on Patentability and Written Opinion of ISA—PCT/IB2009/055140.
New FDA Drug Approval: Patanase (Olopatadine hydrochloride), Center Watch, 2008, 4 pages; http://www.drugs.com/newdrugs/alcon-s-patanase-nasal-approved-fda-nasal-allergy- symptoms-942.html.
Bousquet et al.; "Allergic Rhinitis and Its Impact on Asthma", ARIA Workshop Report, The Journal of Allergy and Clinical Immunology, vol. 108 No. 5, Nov. 2001, 205 pages.
Bousquet et al.; "Allergic Rhinitis and Its Impact on Asthma", (ARIA) 2008 Update (in collaboration with the World ealth Organization, GA2LEN* and AllerGEN**), Allergy 2008, 63, Suppl. 86,: pp. 8-160.
Corren et al.; "Effectiveness of Azelastine Nasal Spray Compared with Oral Cetirizine in Patients with Seasonal Allergic Rhinitis", Clinical Therapeutics, vol. 27, No. 5, May 2005, pp. 543-553.
Berger et al.; "Impact of azelastine nasal spray on symptoms and quality of life compared with cetirizine oral tablets in patients with seasonal allergic rhinitis", vol. 97, Sep. 2006, pp. 375-381.
LaForce et al.; "Efficacy of azelastine nasal spray in seasonal allergic rhinitis patients who remain symptomatic after treatment with fexofenadine", Annals of Allergy, Asthma Immunology, Aug. 2004; 93(2): pp. 154-159, http://www.ncbi.nlm.nih.gov/pubmed/15328675.
Simon et al.; "H1 Antihistiamines: Current Status and Future Directions", World Allergy Organization Journal, 2008, 1:45-155; http://www.waojournal.org/content/1/9/145.
Sherbiny et al.; "Simultaneous determination of loratadine and desloratadine in pharmaceutical preparations using liquid chromatography with a microemulsion as eluent", Science Direct, Journal of Pharmaceutical and Biomedical Analysis, 43, 2007, pp. 1236-1242.
Tzachev et al.; "Comparison of the clinical efficacy of standard and mucoadhesive-based nasal decongestants", 2002, Blackwell Science Ltd., Br. J. Clin Pharmacol, 2002, 53:(1), pp. 107-109.
Horak; "Effectiveness of twice daily azelastine nasal spray in patients with seasonal allergic rhinitis"; Therapeutics and Clinical Risk Management 2008:4(5) pp. 1009-1022; 14 pages.
Bousquet et al.; "Pharmacologic and anti-IgE treatment of allergic rhinitis ARIA update (in collaboration with GA2 LEN)"; Allergy 2006: 61: 1086-1096; 11 pages.

* cited by examiner

*Primary Examiner* — Jean P Cornet
(74) *Attorney, Agent, or Firm* — Salinwanchik, Lloyd & Eisenschenk

(57) ABSTRACT

A pharmaceutical composition comprises a solution having a pH of from 5 to 7.5, including loratadine and/or desloratadine. The composition is suitable for treatment of e.g. allergic rhinitis and allergic conjunctivitis.

3 Claims, No Drawings

PHARMACEUTICAL COMPOSITION FOR TOPICAL APPLICATION

The present invention concerns a pharmaceutical composition for topical application. In particular, the present invention concerns a pharmaceutical composition which is suitable for nasal mucosa administration.

Aqueous pharmaceutical compositions for nasal administration comprising solutions of loratadine are disclosed in WO-A-04082589 and solutions of loratadine and desloratadineare disclosed in WO-A-03101434. The nasal pharmaceutical compositions disclosed in these prior art references comprise relatively low levels of antihistamine in solution.

It is an object of the present invention to provide nasal pharmaceutical compositions which may comprise relatively higher amounts of antihistamine in solution than the prior art solutions but which do not demonstrate increased mucosa irritation.

In accordance with the present invention, there is provided a pharmaceutical composition comprising an aqueous solution having a pH of from 5 to 7.5, preferably from 5 to 7, comprising:

| Component | Amount (wt %) | Example |
|---|---|---|
| a) At least one antihistamine selected from Loratadine and Desloratadine and their pharmaceutically acceptable salts | 0.02-0.1 | |
| b) At least one polyethylene glycol with a molecular weight of from 100 to 600 g/mole (co-solvent) | 5.0-15.0 | PEG 200, PEG 300, PEG 400, PEG 600: PEG 400 is preferred |
| c) Propylene glycol (co-solvent) | 5.0-15.0 | |
| d) At least one non-ionic ethylene oxide/propylene oxide (EO/PO) block copolymer with weight average molecular weight (Mw) from 10,000 to 15,000 (solubilizer) | 1.0-10.0 | Lutrol F127 - (non-ionic EO/PO block copolymer with Mw of about 12,500) |
| e) polyoxyethylene (20) sorbitan monolaurate and/or polyoxyethylene (20) sorbitan monooleate (solubilizer) | 0.5-5.0 | Tween 20, Tween 80: Tween 80 (polyoxyethylene (20) sorbitan monooleate) is preferred |
| f) Stabilizer for antihistamine, preferably a chelator stabilizer | 0.05-0.5 | Salts of EDTA, salts and esters of gallic acid, salts and esters of ascorbic acid, salts of metabisulfite, cysteine and derivatives thereof: Stabilizers which are chelators for the antihistamine are preferred. Alkali salts are preferred e.g. $Na_2EDTA$ |
| Other optional additives | <20 | Sorbitol, glycerine |
| Water | balance to 100.0% | |

Lutrol is a trademark of BASF SE.
Tween is a trademark of Uniquema Americas LLC.

In one embodiment of the present invention, the pharmaceutical composition comprises an aqueous solution having a pH from 5 to 7.5 comprising:

| Component | Amount (wt %) | Example |
|---|---|---|
| Loratadine or a pharmaceutically acceptable salt thereof | 0.02-0.1 | |
| At least one polyethylene glycol with a molecular weight of from 100 to 600 g/mole (co-solvent) | 5.0-15.0 | PEG 200, PEG 300, PEG 400, PEG 600 |
| Propylene glycol (co-solvent) | 5.0-15.0 | |
| At least one non-ionic EO/PO block copolymer with weight average molecular weight (Mw) from 10,000 to 15,000 (solubilizer) | 1.0-10.0 | Lutrol F127 - Mw 12,500 |
| polyoxyethylene (20) sorbitan monolaurate and/or polyoxyethylene (20) sorbitan monooleate (solubilizer) | 0.5-5.0 | Tween 20, Tween 80, |
| Stabilizer | 0.05-0.5 | Salts of EDTA, salts and esters of gallic acid, salts and esters of ascorbic acid, salts of metabisulfite, cysteine and derivatives thereof |
| Other optional additives | <20 | Sorbitol, glycerine |
| Water | balance to 100.0% | |

A particularly preferred pharmaceutical composition of this embodiment comprises an aqueous solution having a pH from 5 to 7 comprising:

| Component | Amount (wt %) |
|---|---|
| Loratadine or salt thereof | 0.06 |
| PEG 400 | 10.0 |
| Propylene glycol | 10.0 |
| At least one non-ionic EO/PO block copolymer with weight average molecular weight (Mw) of about 12,500 | 5.0 |
| Polysorbate 80 | 1.8 |
| $Na_2EDTA$ | 0.1 |
| Water | balance to 100.0% |

In another embodiment of the present invention, the pharmaceutical composition comprises an aqueous solution having a pH from 5 to 7.5 comprising:

| Component | Amount (wt %) | Example |
|---|---|---|
| Desloratadine or a pharmaceutically acceptable salt thereof | 0.02-0.1 | |
| At least one polyethylene glycol with a molecular weight of from 100 to 600 g/mole (co-solvent) | 5.0-15.0 | PEG 200, PEG 300, PEG 400, PEG 600 |
| Propylene glycol (co-solvent) | 5.0-15.0 | |
| At least one non-ionic EO/PO block copolymer with weight average molecular weight (Mw) from 10,000 to 15,000 (solubilizer) | 1.0-10.0 | Lutrol F127 - Mw 12,500 |
| polyoxyethylene (20) sorbitan monolaurate and/or polyoxyethylene (20) sorbitan monooleate (solubilizer) | 0.5-5.0 | Tween 20, Tween 80, |
| Stabilizer | 0.05-0.5 | Salts of EDTA, salts and esters of gallic acid, salts and esters of ascorbic acid, salts of metabisulfite, cysteine and derivatives thereof |
| Other optional additives | <20 | Sorbitol, glycerine |
| Water | balance to 100.0% | |

A particularly preferred pharmaceutical composition of this embodiment comprises an aqueous solution having a pH from 5 to 7 comprising:

| Component | Amount (wt %) |
|---|---|
| Desloratadine or salt thereof | 0.06 |
| PEG 400 | 10.0 |
| Propylene glycol | 10.0 |
| At least one non-ionic EO/PO block copolymer with weight average molecular weight (Mw) 12,500 | 5.0 |
| Polysorbate 80 | 1.8 |
| $Na_2EDTA$ | 0.1 |
| Water | balance to 100.0% |

In comparison to the prior art formulations, by using a combination of the four components b), c), d) and e), pharmaceutical compositions of the present invention contain higher dosage levels of antihistamine in solution but overall lower dosages of potential irritants. For example, if component b) was eliminated, higher levels of component c) would be required to solubilise the antihistamine, and visa-versa: higher levels of b) or c) on their own in the composition causes irritation on the nasal mucosa, which in turn leads to a reduction the time the composition may be effective. Similarly, if component d) was eliminated, higher levels of component e) would be required to solubilise the antihistamine, and visa-versa: higher levels of d) or e) on their own in the composition causes irritation on the nasal mucosa, which in turn leads to a reduction the time the composition may be effective.

The pharmaceutical composition of the present invention may contain, in addition to co-solvents b) and c), one or more other co-solvents, such as sorbitol and glycerine, but such co-solvents should be used at non-irritating levels.

The pharmaceutical composition of the present invention may contain, in addition to co-solubilizers b) and c), one or more other co-solubilizers, but such co-solubilizers should be used at non-irritating levels.

The stabilizer is preferably a chelator for the antihistamine.

The aqueous solution may require pH adjustment to the range 5 to 7.5, preferably 5 to 7. This can be achieved readily by a person skilled in the art. For example, if the pH of the solution is lower than 5, then the pH may be raised by the incorporation of an appropriate amount of alkali, such as NaOH solution.

The pharmaceutical composition is especially suitable for nasal administration, for example for the treatment of allergic rhinitis, though it may also be suitable for ocular administration, for example for the relief of allergic conjunctivitis.

The invention in its various embodiments shall now be further described by way of exemplification only:

A pharmaceutical composition according to the present invention was prepared as follows:

10.0 parts by wt PG (Propylene Glycol) and 10.0 parts by wt $PEG_{400}$ (Macrogol 400) are mixed. The amount of 0.06 parts by wt Loratadine is dissolved in the obtained mixture to obtain Solution A.

Separately, 5.0 parts by wt Lutrol F127 (Poloxamer 407), 1.8 parts by wt Tween 80 (Polysorbate 80) and 0.1 parts by wt $Na_2EDTA$ are dissolved in 70 parts by wt purified water, preheated to 60° C., to obtain Solution B.

Solution A is added to Solution B at constant stirring to obtain Solution C.

Solution C is adjusted as necessary to pH 5,5 with 1M solution of Sodium Hydroxide and is complemented to a total of 100 parts w/w with purified water to obtain the final composition.

The composition is as shown in Table 1.

TABLE 1

| Component | Amount (wt %) | |
|---|---|---|
| Loratadine | 0.06 | active drug |
| PEG 400 | 10.0 | co-solvent |
| PG | 10.0 | co-solvent |
| Lutrol F127 | 5.0 | solubilizer |
| Tween 80 | 1.8 | solubilizer |
| EDTA | 0.1 | stabilizer (chelator) |
| Water | balance to 100.0% | — |

The pharmaceutical composition has the characteristics shown in Table 2:

TABLE 2

| | | |
|---|---|---|
| Appearance | | clear, colorless |
| pH | | 5.5 |
| Density | at 20° C. | $p_s = 1.0273$ |
| | at 25° C. | $p_s = 1.0251$ |
| Dynamic viscosity $\eta$, mPa · s | at 20° C. | $\eta = 54.57 \cdot (2.4100 - 1.0273) \cdot 0.07752 = 5.84$ |
| | at 25° C. | $\eta = 45.93 \cdot (2.4100 - 1.0251) \cdot 0.07752 = 4.93$ |
| Loratadine content | | 0.06 |
| Na$_2$EDTA content | | 0.1 |

The invention claimed is:

1. A pharmaceutical composition for nasal administration wherein said composition is an aqueous solution that consists of:
    a) an antihistamine in an amount between 0.02% and 0.1% of the total weight of the composition (wt %), the antihistamine being selected from the group consisting of loratadine, desloratadine, and pharmaceutically acceptable salts thereof;
    b) polyethylene glycol with a molecular weight between 100 to 600 g/mole in an amount from 5.0 to 15.0 wt %;
    c) a propylene glycol, in an amount from 5.0 to 15.0 wt %;
    d) a non-ionic block copolymer, wherein the block copolymer is an ethylene oxide and propylene oxide block copolymer, and wherein the block copolymer is present in an amount from 1.0 to 10.0 wt %; and
    e) a polyoxyethylene sorbitan monolaurate and/or monooleate, wherein the polyoxyethylene sorbitan monolaurate and/or monooleate is present in an amount from 0.5 to 5.0 wt % and wherein the composition is in an aqueous solution having a pH of from 5 to 7.5.

2. The composition according to claim 1, wherein the antihistamine is loratadine or a pharmaceutically acceptable salt thereof and is present in an amount of 0.06 wt %, the polyethylene glycol is PEG 400 present in an amount of 10 wt %, the propylene glycol is present in an amount of 10.0 wt %, and wherein the block copolymer is present in an amount of 5.0 wt %.

3. The composition of claim 1, wherein the antihistamine is desloratadine or a pharmaceutically acceptable salt thereof and is present in an amount of 0.06 wt %, wherein the polyethylene glycol is PEG 400 present in an amount of 10 wt %, the propylene glycol is present in an amount of 10.0 wt %, and wherein the block copolymer is present in an amount of 5.0 wt %.

* * * * *